United States Patent
Limoge et al.

(10) Patent No.: US 11,889,797 B2
(45) Date of Patent: Feb. 6, 2024

(54) CONTROLLED GROWTH SYSTEM FOR BIOLOGICALS

(71) Applicant: Nanotronics Imaging, Inc., Cuyahoga Falls, OH (US)

(72) Inventors: Damas Limoge, Brooklyn, NY (US); Vadim Pinskiy, Wayne, NJ (US); Parker Musselman, New York, NY (US)

(73) Assignee: Nanotronics Imaging, Inc., Cuyahoga Falls, OH (US)

( * ) Notice: Subject to any disclaimer, the term of this patent is extended or adjusted under 35 U.S.C. 154(b) by 355 days.

(21) Appl. No.: 17/303,620

(22) Filed: Jun. 3, 2021

(65) Prior Publication Data

US 2021/0378190 A1 Dec. 9, 2021

Related U.S. Application Data

(60) Provisional application No. 63/034,027, filed on Jun. 3, 2020.

(51) Int. Cl.
*A01G 18/00* (2018.01)
*A01G 9/24* (2006.01)
(Continued)

(52) U.S. Cl.
CPC ............... *A01G 31/04* (2013.01); *A01G 2/00* (2018.02); *A01G 31/06* (2013.01); *G05B 13/024* (2013.01); *A01G 2031/006* (2013.01)

(58) Field of Classification Search
CPC .......... A01G 9/24; A01G 18/69; A01G 18/00; A01G 18/60
See application file for complete search history.

(56) References Cited

U.S. PATENT DOCUMENTS 6,567,537 B1 5/2003 Anderson
7,987,632 B2 8/2011 May et al.
(Continued)

FOREIGN PATENT DOCUMENTS

JP 2014-110795 6/2014
WO 2018100917 6/2018
(Continued)

OTHER PUBLICATIONS

PCT International Application No. PCT/US21/35686, International Search Report and Written Opinion of the International Searching Authority, dated Sep. 24, 2021, 13 pages.
(Continued)

*Primary Examiner* — Monica L Perry
(74) *Attorney, Agent, or Firm* — DLA PIPER LLP (US)

(57) ABSTRACT

A controlled growth system is provided herein. The controlled growth system includes a controlled growth environment, a controller, a sensor, and a computing system. The controlled growth environment is configured to grow a biologic. The controller is in communication with the controlled growth environment. The controller is configured to manage process parameters of the controlled growth environment. The sensor is configured to monitor the biologic during a growth process. The computing system is in communication with the sensor and the controller. The computing system is programmed to perform operations for achieving a desired final quality metric for the biologic.

20 Claims, 5 Drawing Sheets

(51) Int. Cl.
*A01G 31/04* (2006.01)
*A01G 2/00* (2018.01)
*G05B 13/02* (2006.01)
*A01G 31/06* (2006.01)
*A01G 31/00* (2018.01)

(56) References Cited

U.S. PATENT DOCUMENTS

| | | | |
|---|---|---|---|
| 9,730,394 | B2 | 8/2017 | Van De Vegte et al. |
| 10,986,789 | B1* | 4/2021 | Roberts ............... A01G 9/26 |
| 2020/0184153 | A1* | 6/2020 | Bongartz ............... A01G 9/24 |
| 2021/0100173 | A1* | 4/2021 | Khwaja ............... H05B 45/12 |
| 2022/0122007 | A1* | 4/2022 | Sasaki ............... G06Q 10/063 |

FOREIGN PATENT DOCUMENTS

| | | |
|---|---|---|
| WO | 2018101004 | 6/2018 |
| WO | 2019082617 | 5/2019 |
| WO | 2019099474 | 5/2019 |
| WO | 2020012616 | 1/2020 |
| WO | 2020/034039 | 2/2020 |
| WO | 2020049182 | 3/2020 |
| WO | 2020086907 | 4/2020 |
| WO | 2020106743 | 5/2020 |

OTHER PUBLICATIONS

Office Action for Japanese Patent Application No. 2022-573678, dated Nov. 10, 2023, 16 pages.

* cited by examiner

CONTROLLED GROWTH SYSTEM FOR BIOLOGICALS

CROSS-REFERENCE TO RELATED APPLICATIONS

This application claims priority to U.S. application Ser. No. 63/034,027, filed Jun. 3, 2020, which is hereby incorporated by reference in its entirety.

FIELD OF THE DISCLOSURE

The present disclosure generally relates to a system and method for biological growth within a controlled growth environment.

BACKGROUND

There exist many industries for which biologics represents possible alternatives with significant benefits for a variety of applications. For example, lab-grown or manufactured mycelium has a variety of applications, such as ecologically friendlier and safer production of leather, biodegradable packaging and temporary construction materials, lab-grown meat alternatives and the like. Similarly, cannabis has shown to provide various medical benefits as adoption of cannabis as a medical treatment has grown in frequency.

SUMMARY

In embodiments, a controlled growth system is disclosed herein. The controlled growth system includes a controller, a sensor, and a computing system. The controlled growth environment is configured to grow a biologic. The controller is configured to manage process parameters of a controlled growth environment. The sensor is configured to monitor a biologic in the controlled growth environment during a growth process. The computing system is in communication with the sensor and the controller. The computing system is programmed to perform operations. The operations include initiating the growth process by providing the controller with an initial set of process parameters for the controlled growth environment. The operations further include receiving sensor data from the sensor during the growth process. The sensor data includes at least an image of the biologic. The operations further include generating, based on the image, a predicted final quality metric for the biologic. The predicted final quality metric represents a final state of the biologic at an end of the growth process based on a current state of the biologic. The operations further include determining that the predicted final quality metric for the biologic is not within a threshold range of a canonical final quality metric. The operations further include, based on the determining, generating an updated set of process parameters to achieve the canonical final quality metric. The operations further include providing the updated set of process parameters to the controller.

In some embodiments a method for controlling a growth of a biologic in a controlled growth environment is disclosed herein. A computing system initiates a growth process for the biologic in the controlled growth environment by providing a controller of the controlled growth environment with an initial set of process parameters. The computing system receives sensor data from a sensor of the controlled growth environment during the growth process. The sensor data includes at least an image of the biologic. The computing system generates, based on the image, a predicted final quality metric for the biologic. The predicted final quality metric represents a final state of the biologic at an end of the growth process based on a current state of the biologic. The computing system determines that the predicted final quality metric for the biologic is not within a threshold range of a canonical final quality metric. Based on the determining, the computing system generates an updated set of process parameters to achieve the canonical final quality metric. The computing system provides the updated set of process parameters to the controller.

In some embodiments, a controlled growth system for mycelium is disclosed herein. The controlled growth system includes a sensor and a computing system. The sensor is configured to monitor a mycelium sheet in a controlled growth environment during a growth process. The computing system in communication with the sensor and the controlled growth environment. The computing system is programmed to perform operations. The operations include initiating the growth process by providing the controlled growth environment with an initial set of process parameters for the controlled growth environment. The operations further include receiving sensor data from the sensor during the growth process. The sensor data includes at least an image of the mycelium sheet. The operations further include generating, based on the image, a predicted final quality metric for the mycelium sheet. The predicted final quality metric represents a final state of the mycelium sheet at an end of the growth process based on a current state of the mycelium sheet. The operations further include determining that the predicted final quality metric for the mycelium sheet is not within a threshold range of a canonical final quality metric. The operations further include, based on the determining, generating an updated set of process parameters to achieve the canonical final quality metric. The operations further include adjusting the controlled growth environment based on the updated set of process parameters.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting in their scope, the principles herein are described and explained with additional specificity and detail through the use of the accompanying drawings in which.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

One or more techniques provided herein are directed to a controlled growth system. The controlled growth system includes a controller, a sensor, and a computing system. The controlled growth environment is configured to grow a biologic. The controller is configured to manage process parameters of a controlled growth environment. The sensor is configured to monitor a biologic in the controlled growth environment during a growth process. The computing system is in communication with the sensor and the controller. The computing system is programmed to perform operations for achieving a desired final quality metric for the biologic.

Figure 1:
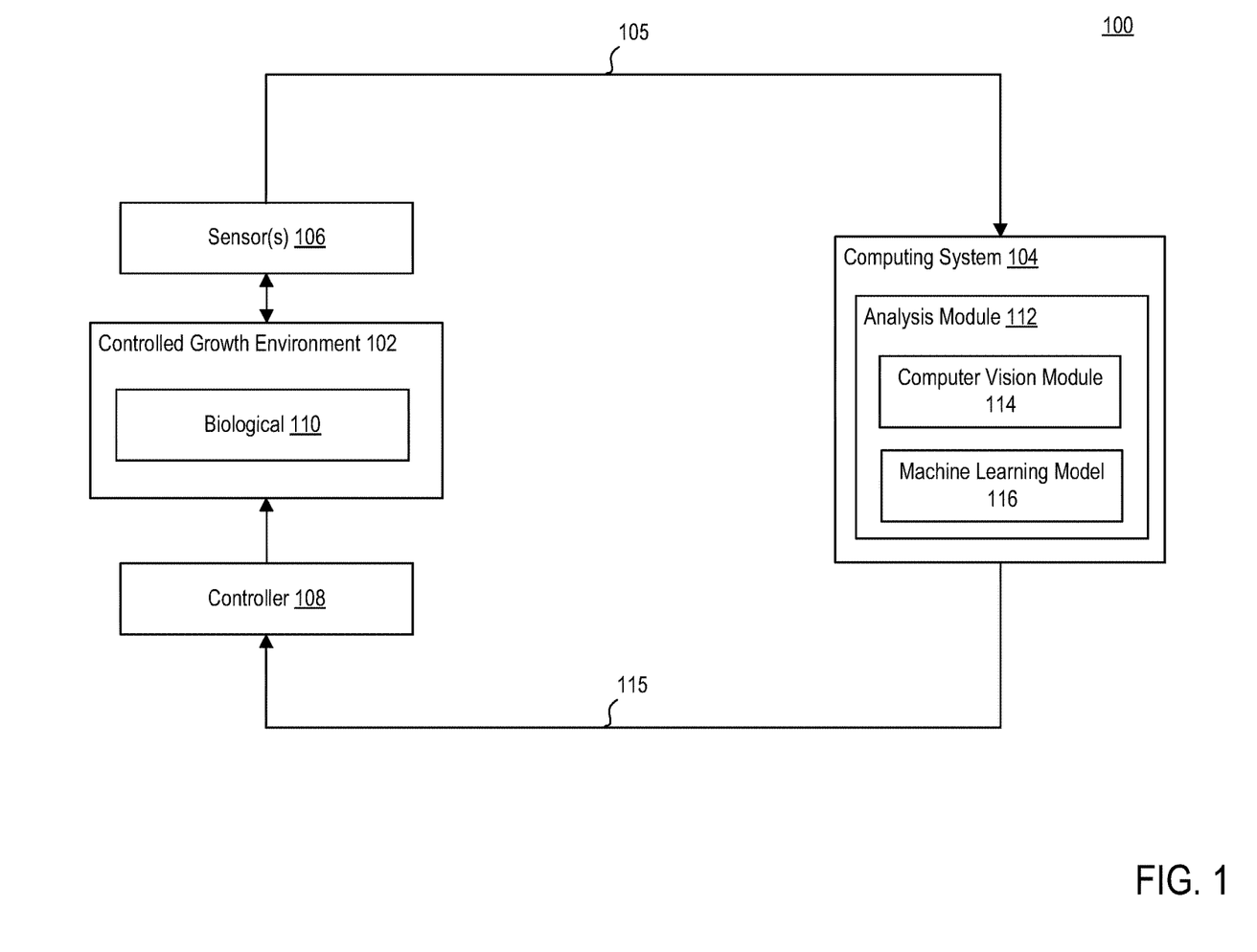
FIG. 1 is a block diagram illustrating a computing environment, according to example embodiments.

FIG. 1 is a block diagram illustrating a computing environment 100, according to example embodiments. As shown, computing environment 100 may include a controlled growth environment 102, a computing system 104, a sensor 106, and a controller 108 communicating via one or more communication links 105 and 115.

In some embodiments, one or more communication links 105 and 115 may be hardwired communication links. In some embodiments, one or more communication links 105 and/or 115 may be of any suitable type, including individual connections via the Internet, such as cellular or Wi-Fi networks. In some embodiments, communication link 105 and/or communication link 115 may connect terminals, services, and mobile devices using direct connections, such as radio frequency identification (RFID), near-field communication (NFC), Bluetooth™, low-energy Bluetooth™ (BLE), Wi-Fi™, ZigBee™, ambient backscatter communication (ABC) protocols, USB, WAN, or LAN. Because the information transmitted may be personal or confidential, security concerns may dictate one or more of these types of connection be encrypted or otherwise secured. In some embodiments, however, the information being transmitted may be less personal, and therefore, the network connections may be selected for convenience over security.

Communication link 105 and/or communication link 115 may include any type of computer networking arrangement used to exchange data or information. For example, communication link 105 and/or communication link 115 may be the Internet, a private data network, virtual private network using a public network and/or other suitable connection(s) that enables components in computing environment 100 to send and receive information between the components of environment 100.

Controlled growth environment 102 may be representative of a growing structure for growing a biologic 110. For example, controlled growth environment 102 may be configured to provide and/or maintain optimal growing conditions for biologic 110. Exemplary biologics 110 may include, but are not limited to, mycelium, cannabis, consumer produce, algae, soy, cyanobacteria, DNA, synthetic proteins, and the like. Controlled growth environment 102 may ensure that biologic 110 is provided with adequate conditions for growth. For example, controller 108, in communication with controlled growth environment 102, may control one or more variables for maintain an ideal or optimal growing environment within controlled growth environment 102. In some embodiments, controller 108 may be configured to control and/or modulate one or more of temperature, humidity, light intensity, pH levels, carbon dioxide levels, soil nitrates, direct irrigation flow, oxygen levels, environmental air flow volume and direction, ambient noise frequency content, seed patterning and density, harvesting schedule, light direction, and the like. By controlling one or more variables, controller 108 may assist in achieving a desired final quality metric. For example, controller 108 may assist in achieving a desired growth uniformity of biologic 110.

To determine whether biologic 110 is progressing to a desired final quality metric, controlled growth environment 102 may utilize a process control system. For example, sensors 106 may be configured to monitor growth of biologic 110 within controlled growth environment 102. In some embodiments, sensors 106 may include an imaging device (e.g., a camera) configured to capture one or more images of biologic 110 at various stages of the growth process. In some embodiments, sensors 106 may include various sensors to measure various variables associated with the growth process. For example, sensors 106 may include, but are not limited to, a temperature sensor, a humidity sensor, a light intensity sensor, a carbon dioxide sensor, and the like. Sensors 106 may be configured to provide one or more images and/or one or more measurements to computing system 104 for analysis.

Computing system 104 may be configured to analyze the one or more images and/or the one or more measurements to project or predict a final quality metric for biologic 110. Based on the predicted final quality metric, computing system 104 may cause controller 108 to adjust processing parameters of controlled growth environment 102. For example, based on the predicted final quality metric, computing system 104 may cause controller 108 to adjust one or more of a temperature, humidity, light intensity, carbon dioxide, etc. of one or more portions of controlled growth environment 102.

As shown, computing system 104 may include analysis module 112. Analysis module 112 may be comprised of one or more software modules. The one or more software modules may be collections of code or instructions stored on a media (e.g., memory of computing system 104) that represent a series of machine instructions (e.g., program code) that implement one or more algorithmic steps. Such machine instructions may be the actual computer code the processor of computing system 104 interprets to implement the instructions or, alternatively, may be a higher level of coding of the instructions that is interpreted to obtain the actual computer code. The one or more software modules may also include one or more hardware components. One or more aspects of an example algorithm may be performed by the hardware components (e.g., circuitry) itself, rather as a result of the instructions.

Analysis module 112 may be configured to analyze the data received from sensors 106. For example, analysis module 112 may be configured to analyze the one or more images captured from sensors 106 to project or predict a final quality metric for biologic 110. A final quality metric may broadly refer to a final quality attribute of biologic 110 after biologic 110 undergoes its controlled growth environment. In some embodiments, a final quality metric may correspond to a level of uniformity across a growth of a mycelium sheet. In some embodiments, exemplary final quality metrics may not be limited to level of uniformity and may include one or more of height/shape/volume, color/irradiance, chemical composition, off-gassing composition, codification of human judgement (e.g. classification of plants using human generated labels), rate of change of quality metrics mentioned above, aggregation of metrics mentioned above, and the like. Generally, a final quality metric is one that cannot be directly measured during the growth process. Instead, it is inferred or predicted given the current state of biologic 110 and analysis module's 112 knowledge of similar processes. Using such analysis, an administrator may determine whether biologic 110 has experienced a fatal error (i.e., based on the analysis, biologic 110 cannot achieve the desired final quality metric), is in-line to achieve the desired final quality metric (i.e., no adjustments need to be made to controlled growth environment 102), or is out-of-line with the desired final quality metric and requires process parameter adjustments.

In some embodiments, analysis module 112 may include computer vision module 114. Computer vision module 114 may be configured to analyze the one or more images captured by sensor 106. Based on the analyzed images, analysis module 112 may predict or generate a final quality metric for biologic 110. In some embodiments, to analyze the one or more images, computer vision module 114 may employ a topographic analysis approach. For example, computer vision module 114 may utilize an algorithmic analysis of a three-dimensional point cloud based on the one or more images captured by sensor 106. Such analysis may aid analysis module 112 in determining whether adjustments to processing parameters of controlled growth environment 102 are needed to achieve the desired final quality metric.

In some embodiments, analysis module 112 may include machine learning model 116. Machine learning model 116 may be representative of a convolutional neural network trained to analyze images captured by sensors 106 to predict or project a final quality metric of biologic 110. In some embodiments, machine learning model 116 may undergo a training process, in which machine learning model 116 is provided with a training set that includes, but is not limited to, images of a biologic and process parameters of controlled growth environment 102 corresponding to each image. In this manner, machine learning model 116 may be trained to learn how various processing parameters affect a final quality metric of a biologic at various stages of the growing process. In this manner, analysis module 112 may leverage machine learning model 116 to optimize or adjust processing parameters of controlled growth environment 102, such that controlled growth environment 102 can achieve the desired final quality metric for biologic 110.

Once analysis module 112 determines that processing parameters of controlled growth environment 102 should be adjusted to achieve the desired quality metric, analysis module 112 may instruct controller 108 to adjust the processing parameters of controlled growth environment 102 accordingly. In this manner, computing environment 100 may include a feedback loop in which growth of biologic 110 is constantly monitored and adjusted, such that controlled growth environment 102 may achieve the desired final quality metric.

Figure 2:
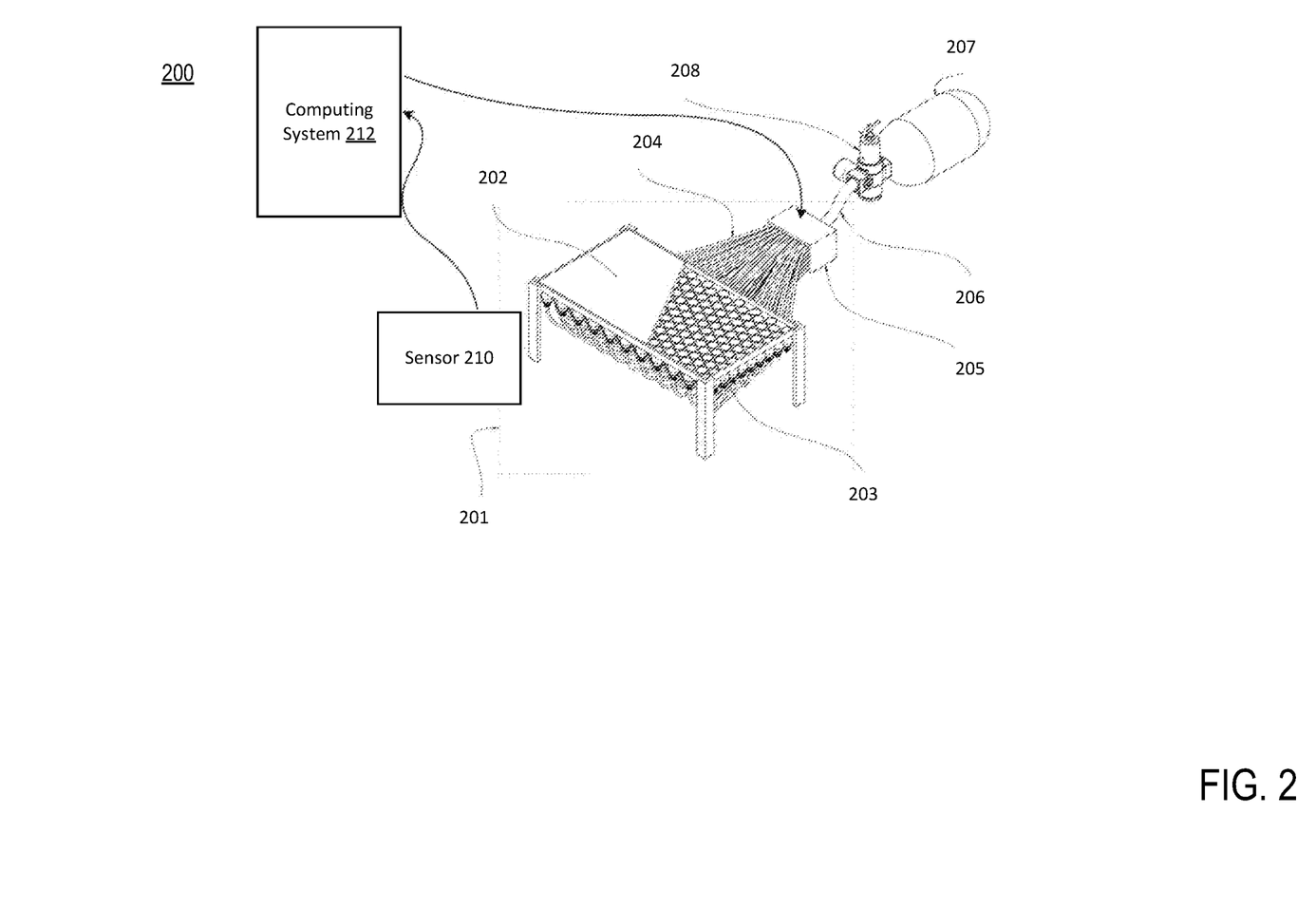
FIG. 2 is a block diagram illustrating a computing environment, according to example embodiments.

FIG. 2 is a block diagram illustrating a computing environment 200, according to example embodiments. Computing environment 200 may represent a specific use-case of computing environment 100. For example, computing environment 200 may represent an environment for growing mycelium sheets.

As shown, computing environment 200 may include controlled growth environment 201, mycelium sheet 202, column tray 203, supply tube bundle 204, programmable manifold 205, feed tube 206, carbon dioxide supply tank 207, carbon dioxide pressure regulator 208, sensor 210, and computing system 212.

As provided, computing environment 200 may be used to grow a mycelium sheet. Generally, there exists many industries for which mycelium (the vegetative portion of a fungus such as that in mushrooms) represents a possible alternative with significant benefits. For example, the use of lab-grown or manufactured mycelium include such things as ecologically friendlier and safer production of leather, biodegradable packaging, temporary construction materials, lab-grown meat alternatives, and the like. Growing mycelium may be accomplished by introducing an initial mixture into a set mold by compressing mycelium into a desired shape, griding mycelium fibers into a mixture used in or alongside other processes, or by physically shaping and removing excess mycelium from a mat of mycelium. In one or more embodiments, there may be additional processing steps to normalize a mycelium sheet such that deformities from the initial growth do not propagate into the final product. Computing environment 200 may be configured to monitor growth of mycelium to detect or catch deformities early in the growth process and correct them, such that a desired final quality metric for the mycelium can be achieved.

As shown in FIG. 2, a mycelium sheet 202 may be grown upon a column tray 203 inside controlled growth environment 201. Each column of column tray 203 may be individually controlled by programmable manifold 205. Each column of column tray 203 may be fed a gas mixture, as controlled by programmable manifold 205, to control for localized variations associated with each column. In some embodiments, manifold 205 may receive instructions from computing system 212. For example, computing system 212 may include an analysis module 214 (similarly configured as analysis module 112) configured to analyze the current growth state of mycelium sheet 202, as well as other related factors (e.g., temperature, humidity, light intensity, etc.), in order to update a gas flow rate at each column. Adjusting the gas flow rate of each column may account for regions of mycelium sheet 202 that may have too much grown (e.g., a localized region that is too thick) or too little growth (e.g., a localized region that is too thin) relative to the growth for the entirety of mycelium sheet 202. In some embodiments, the defined growth may be based on an average or median growth for the entire sheet. Analysis module 214 may be configured to analyze the growth state of the mycelium state using one or more machine learning and/or computer vision approaches. For example, a machine learning model (e.g., convolutional neural network) may be trained on the effects of gas flow rates upon localized regions. By manipulating various growth factors, analysis module 214 can help achieve a desired final quality metric, e.g., a uniform sheet of mycelium.

As shown, mycelium sheet 202 may grow from a tray formed by tops of a column tray 203 positioned in controlled growth environment 201. Controlled growth environment 201 may include supply tubes 204 for feeding each column of column tray 203. Supply tubes 204 may be coupled to programmable manifold 205, which may be fed by a carbon dioxide ($CO_2$) regulator 208 controlling an overall throughput of carbon dioxide from supply tank 207.

In some embodiments, the final product to be formed, i.e., a sheet of mycelium, may grow from column tray 203. Column tray 203 may be scaled arbitrarily, such that a given construction of this apparatus may create a sheet of any length or width.

Figure 3:
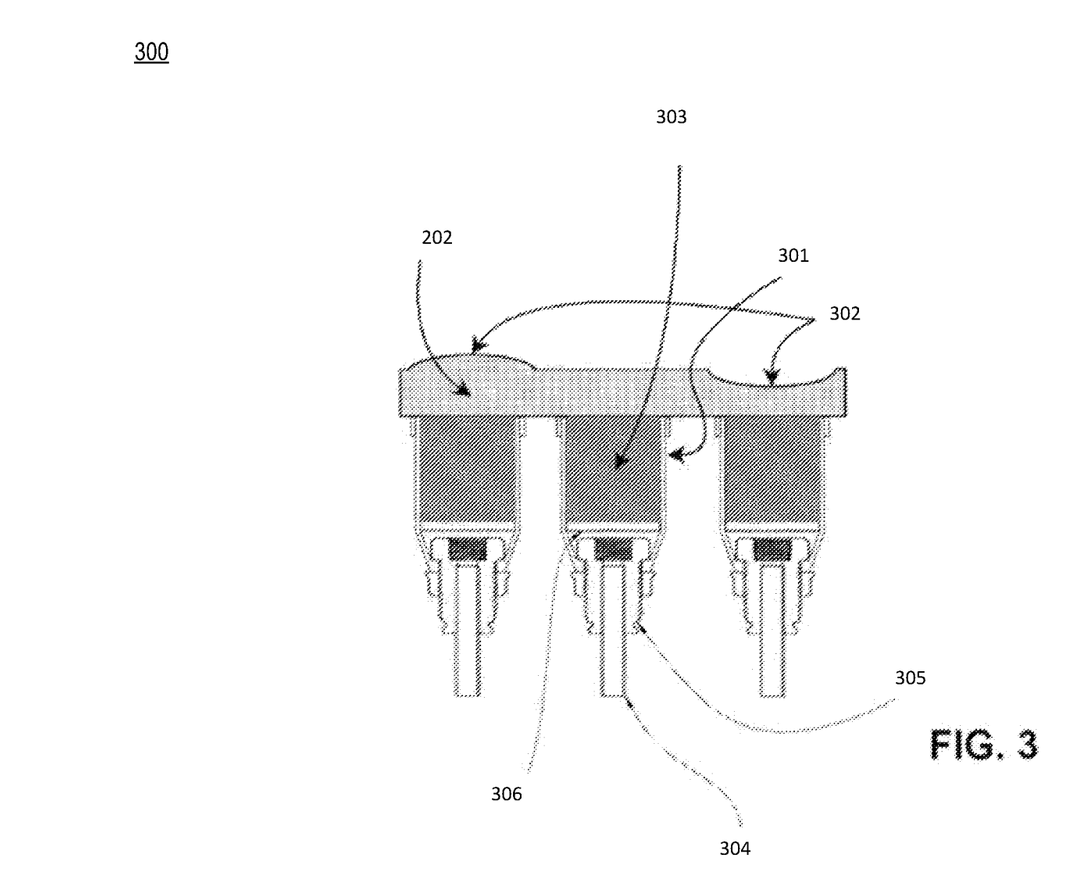
FIG. 3 illustrates example column control elements of a column tray, according to example embodiments.

FIG. 3 illustrates example column control elements of column tray 203, according to example embodiments. As provided above, the sheet of mycelium may be grown from column tray 203 containing a bulk substrate and/or spawn mixture for the chosen fungus to grow from. In some embodiments, the precise shape (e.g., cylindrical, rectangular prism, hexagonal prism, etc.) and size of columns may vary. Depending on the structure of the columns, space may or may not exist between the surface regions of adjacent columns for mycelium sheet 202 to grow over. In some embodiments, mycelium of the same species may be known to grow together to form a singular organism. Bridges may form over gaps, as the mat or sheet grows in thickness. If there are small gaps between columns, they may slowly have less of an impact on the overall sheet structure.

As provided in FIG. 3, there are several columns with space between them. FIG. 3 may provide how mycelium may grow or join together to form a single mycelium sheet 202 atop each individual column 301 of column tray 203.

Each column 301 from column tray 203 may be connected at the based via a one-way valve to a single supply tube 204 that, together, may be bundled and attached to programmable manifold 205. Programmable manifold 205 may be fed by a tube from regulator 208 attached to carbon dioxide supply tank 207. In some embodiments, carbon dioxide supply tank 207 may be inside controlled growth environment 201. In some embodiments, carbon dioxide supply tank 207 may be external to controlled growth environment 201.

A source of carbon dioxide may provide an example way to control the growth rate of mycelium sheet 202. The fungus chosen for this example may be one that exhibits reduced growth rate in the presence of carbon dioxide. As those skilled in the art recognize, other gas and fungi combinations may be used without departing from the present techniques. Pressure regulator 208 may control the overall flow rate to programmable manifold 205. In some embodiments, programmable manifold 205 may allow for multiple different gas supply tanks to be used, thus providing the ability to mix gases as desired.

Each column 301 from column tray 203 may include a localize variation 302 and may connect to one supply tube 304, feeding that column 301 through an inlet nozzle. Although the precise structure of columns 301 may vary, each column 301 may include a bulk and spawn substrate mixture 303 upon which mycelium sheet 202 may grow. With the walls and bottom of column 301 closed, the fungus may grow a mycelium layer on the open top layer forming the mycelium sheet 202 atop and between adjacent columns 301. These columns 301 may be directly adjacent to each other or separated, as shown in FIG. 3. Mycelium sheet 202 may grow above and cover any gaps between columns 301.

Due to chaotic effects, mycelium drawing nutrients from any singular column 301 may or may not grow faster or slower than others. As such, localized variations may appear in mycelium sheet 202 where some regions will be thicker or thinner than others; a region of increased growth and a region with depressed growth are illustrated in FIG. 3

Bulk and spawn substrate mixture may start, for example, as a 10-to-1 bulk-to-spore or other ratio allowing for quick germination of the fungus into mycelium sheet 202. The ratio of bulk to spawn substrate, and choice of species of fungus, may vary without departing form the present techniques disclosed herein. This may be the location from which mycelium sheet 202 begins its initial growth. Depending on implementation, the bulk and spawn substrate mixture may or may not need to be replaced for each new mycelium sheet 202 to be grown.

In some embodiments, gas flowing through manifold 205 may be directly fed to each column 301 through an inlet nozzle 305. This may provide a local gradient or concentration of gas at the location of each column 301, such that mycelium sheet 202 above or at each column 301 may be controlled to grow faster or slower, based on the gas provided through supply tube.

In some embodiments, the structure of inlet nozzle 305 may facilitate gas supply tube 304 being connected to column 301 without leakage and a presence of a particulate filter 306. Particulate filter 306 may be used to prevent bulk and spawn substrate mixture 303 from clogging supply tube 304 and/or nozzle 305. Particulate filter 306 may achieve this by isolating the growing matter from gas delivery system.

Figure 4:
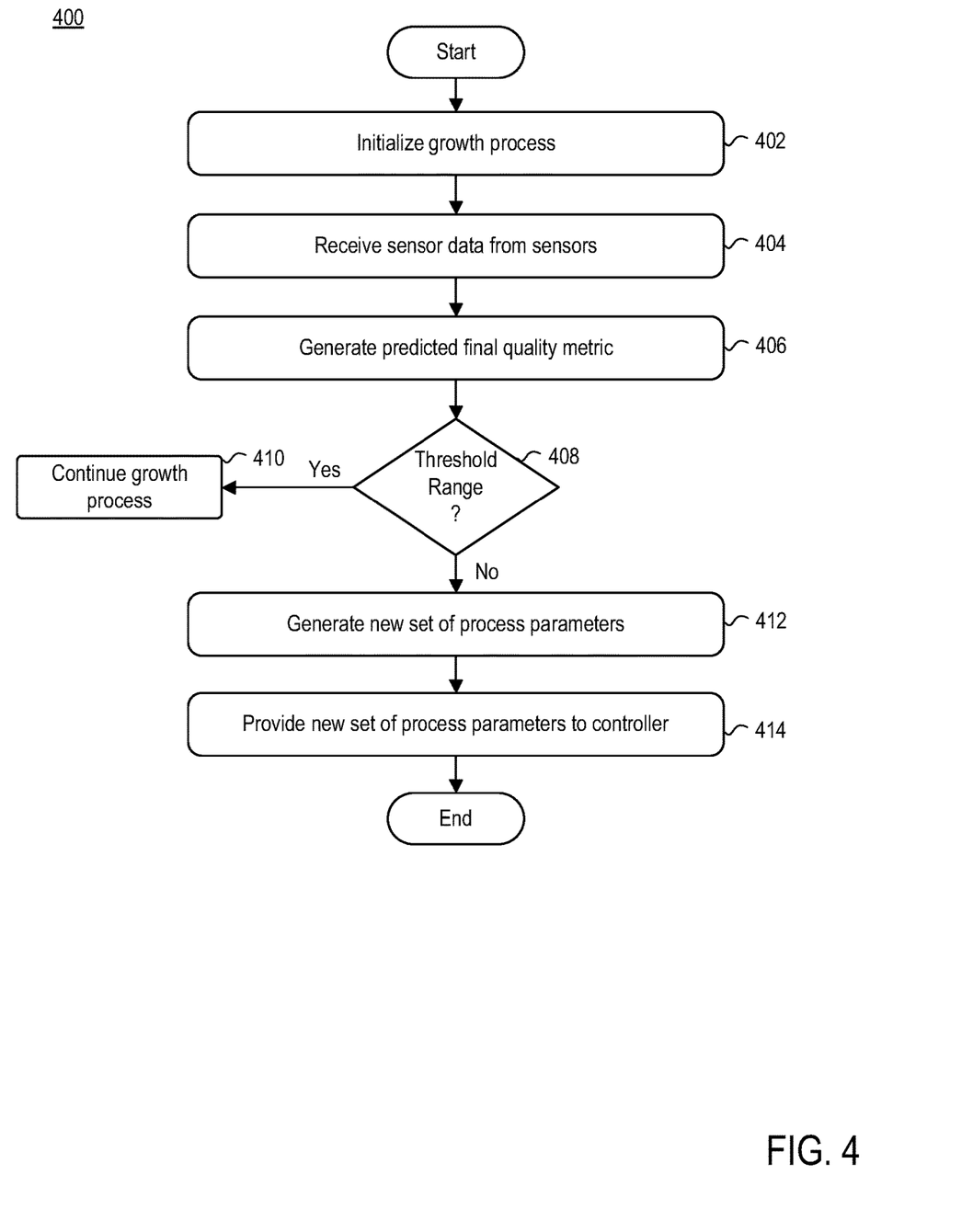
FIG. 4 is a flow diagram illustrating a method of growing a biologic in a controlled growth environment, according to example embodiments.

FIG. 4 is a flow diagram illustrating a method 400 of growing a biologic in a controlled growth environment, according to example embodiments. For example, method 400 may correspond to functionality implemented within computing environment 100. Method 400 may begin as step 402.

At step 402, a growth process may be initiated. For example, an administrator may initiate a growth process for biologic 110 within controlled growth environment 201. Initiating the growth process for biologic 110 may include computing system 104 communicating an initial set of process parameters to controller 108. For example, computing system 104 may set an initial set of process parameters that include, but are not limited to, a temperature, humidity level, light intensity, water level, water frequency, carbon dioxide level, and the like for one or more portions of controlled growth environment 201.

At step 404, computing system 104 may receive sensor data from sensors 106. For example, during the growing process, computing system 104 may periodically, in real-time, or on-demand receive sensor data from sensors 106. In some embodiments, the sensor data may include at least one or more images of biologic 110 captured by sensors 106. In some embodiments the sensor data may further include one or more of a temperature reading, a humidity reading, a light intensity reading, a carbon dioxide level reading, and the like.

At step 406, computing system 104 may generate a predicted final quality metric for biologic 110 based at least on the one or more images of biologic 110 captured by sensors 106. For example, analysis module 112 may analyze the data received from sensors 106 to determine a predicted final quality metric based on the current state of biologic 110. A final quality metric may broadly refer to a final quality attribute of biologic 110 after biologic 110 undergoes its controlled growth environment. In some embodiments, a final quality metric may correspond to a level of uniformity across a growth of a mycelium sheet.

In some embodiments, to generate the predicted final quality metric, analysis module 112 may utilize computer vision module 114. Computer vision module 114 may analyze the one or more images captured by sensor 106 to predict or generate a final quality metric for biologic 110. In some embodiments, to analyze the one or more images, computer vision module 114 may employ a topographic analysis approach. For example, computer vision module 114 may utilize an algorithmic analysis of a three-dimensional point cloud based on the one or more images captured by sensor 106.

In some embodiments, to generate the predicted final quality metric, analysis module 112 may utilize machine learning model 116. Machine learning model 116 may analyze images captured by sensors 106 to predict or project the final quality metric of biologic 110. For example, based on the training process, machine learning model 116 may identify the current state biologic 110 and current processing parameters to determine the final quality metric, based on the current path of growth.

At step 408, computing system 104 may determine whether the predicted final quality metric is within an acceptable range of values. For example, computing system 104 may compare the predicted final quality metric to a canonical final quality metric to determine whether processing parameters of controlled growth environment 102 need to be adjusted. If, at step 408, computing system 104 determines that the predicted final quality metric is within an acceptable range, then at step 410, the growth process continues uninterrupted.

If, however, at step 408, computing system 104 determines that the predicted final quality metric is not within the acceptable range, then at step 412, computing system 104 may determine a new set of process parameters for controlled growth environment that will help achieve or lead to a growth that falls within the acceptable range. For example, analysis module 112 may leverage output from computer vision module 114 and/or machine learning model 116 to optimize or adjust processing parameters of controlled growth environment 102, such that controlled growth environment 102 can achieve the desired final quality metric for biologic 110.

At step 414, computing system 104 may provide the updated process parameters to controller 108 for implementation.

In some embodiments, such as those for mycelium sheets, updated processing parameters may include a flow rate of carbon dioxide for individual columns 301 in column tray 203. In this manner, computing system 104 may account for differences in growth rate across mycelium sheet 202 such that a uniform mycelium sheet 202 may be achieved.

As those skilled in the art recognize, the above processed may be carried out throughout the growth cycle of biologic 110. In this manner, computing system 104 may continually adjust processing parameters of controlled growth environment 102 to achieve the desired final quality metric.

Figure 5A:
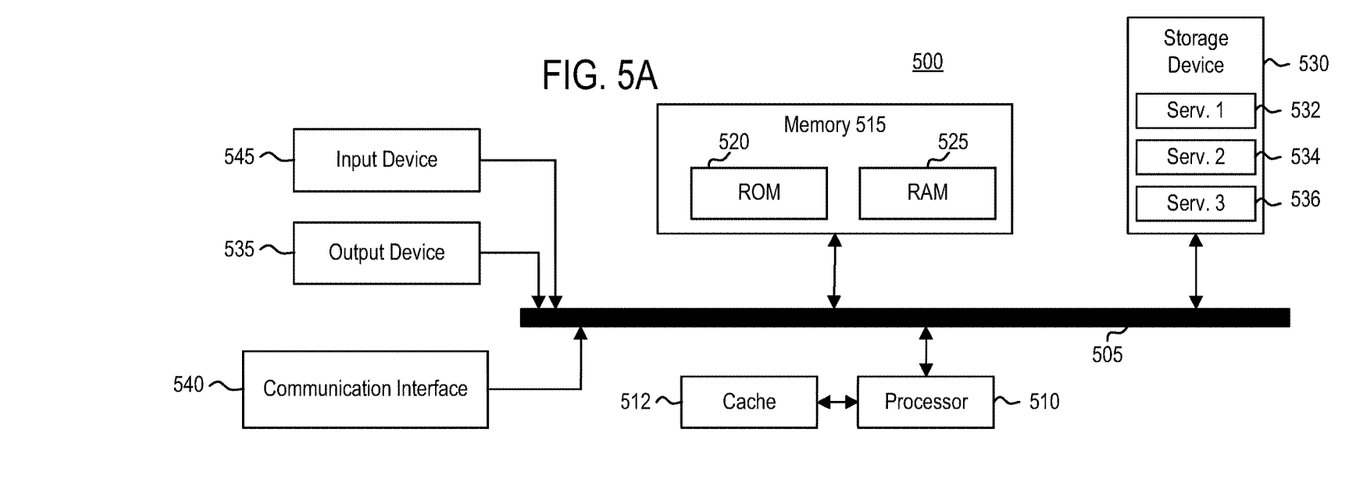
FIG. 5A illustrates a system bus computing system architecture, according to example embodiments.

FIG. 5A illustrates an architecture of system bus computing system 500, according to example embodiments. One or more components of system 500 may be in electrical communication with each other using a bus 505. System 500 may include a processor (e.g., one or more CPUs, GPUs or other types of processors) 510 and a system bus 505 that couples various system components including the system memory 515, such as read only memory (ROM) 520 and random access memory (RAM) 525, to processor 510. System 500 can include a cache of high-speed memory connected directly with, in close proximity to, or integrated as part of processor 510. System 500 can copy data from memory 515 and/or storage device 530 to cache 512 for quick access by processor 510. In this way, cache 512 may provide a performance boost that avoids processor 510 delays while waiting for data. These and other modules can control or be configured to control processor 510 to perform various actions. Other system memory 515 may be available for use as well. Memory 515 may include multiple different types of memory with different performance characteristics. Processor 510 may be representative of a single processor or multiple processors. Processor 510 can include one or more of a general purpose processor or a hardware module or software module, such as service 1 532, service 2 534, and service 5 536 stored in storage device 530, configured to control processor 510, as well as a special-purpose processor where software instructions are incorporated into the actual processor design. Processor 510 may essentially be a completely self-contained computing system, containing multiple cores or processors, a bus, memory controller, cache, etc. A multi-core processor may be symmetric or asymmetric.

To enable user interaction with the system 500, an input device 545 which can be any number of input mechanisms, such as a microphone for speech, a touch-sensitive screen for gesture or graphical input, keyboard, mouse, motion input, speech and so forth. An output device 535 (e.g., a display) can also be one or more of a number of output mechanisms known to those of skill in the art. In some instances, multimodal systems can enable a user to provide multiple types of input to communicate with system 500. Communications interface 540 can generally govern and manage the user input and system output. There is no restriction on operating on any particular hardware arrangement and therefore the basic features here may easily be substituted for improved hardware or firmware arrangements as they are developed.

Storage device 530 may be a non-volatile memory and can be a hard disk or other types of computer readable media that can store data that are accessible by a computer, such as magnetic cassettes, flash memory cards, solid state memory devices, digital versatile disks, cartridges, random access memories (RAMs) 525, read only memory (ROM) 520, and hybrids thereof.

Storage device 530 can include services 532, 534, and 536 for controlling the processor 510. Other hardware or software modules are contemplated. Storage device 530 can be connected to system bus 505. In one aspect, a hardware module that performs a particular function can include the software component stored in a computer-readable medium in connection with the necessary hardware components, such as processor 510, bus 505, output device 535 (e.g., a display), and so forth, to carry out the function.

Figure 5B:
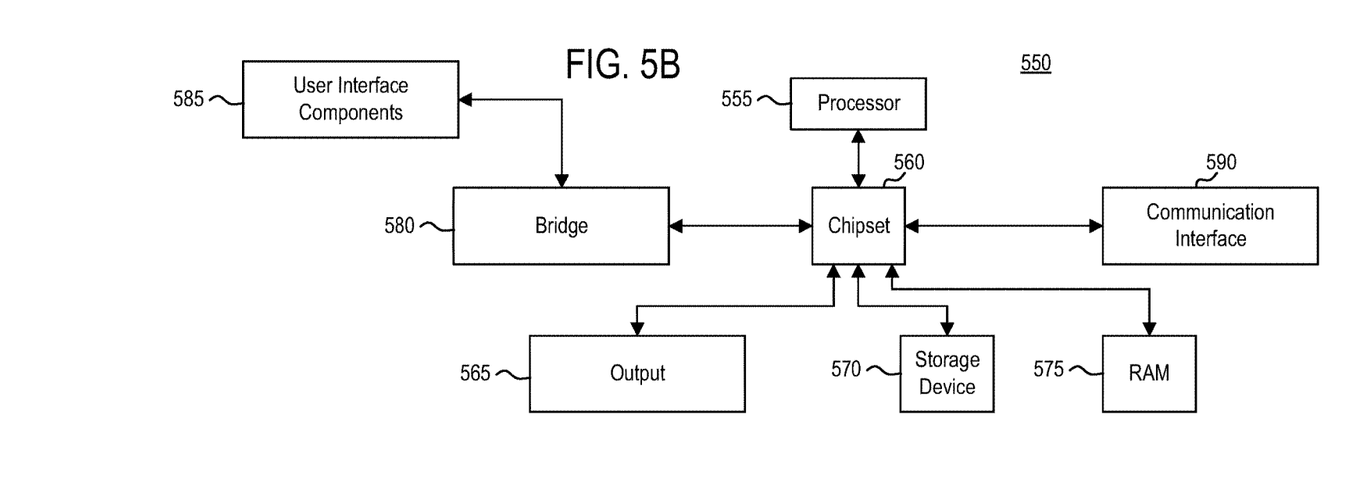
FIG. 5B illustrates a computer system having a chipset architecture, according to example embodiments.

FIG. 5B illustrates a computer system 550 having a chipset architecture, according to example embodiments. Computer system 550 may be an example of computer hardware, software, and firmware that can be used to implement the disclosed technology. System 550 can include one or more processors 555, representative of any number of physically and/or logically distinct resources capable of executing software, firmware, and hardware configured to perform identified computations. One or more processors 555 can communicate with a chipset 560 that can control input to and output from one or more processors 555. In this example, chipset 560 outputs information to output 565, such as a display, and can read and write information to storage device 570, which can include magnetic media, and solid-state media, for example. Chipset 560 can also read data from and write data to storage device 575 (e.g., RAM). A bridge 580 for interfacing with a variety of user interface components 585 can be provided for interfacing with chipset 560. Such user interface components 585 can include a keyboard, a microphone, touch detection and processing circuitry, a pointing device, such as a mouse, and so on. In general, inputs to system 550 can come from any of a variety of sources, machine generated and/or human generated.

Chipset 560 can also interface with one or more communication interfaces 590 that can have different physical interfaces. Such communication interfaces can include interfaces for wired and wireless local area networks, for broadband wireless networks, as well as personal area networks. Some applications of the methods for generating, displaying, and using the GUI disclosed herein can include receiving ordered datasets over the physical interface or be generated by the machine itself by one or more processors 555 analyzing data stored in storage device 570 or 575. Further, the machine can receive inputs from a user through user interface components 585 and execute appropriate functions, such as browsing functions by interpreting these inputs using one or more processors 555.

It can be appreciated that example systems 500 and 550 can have more than one processor 510 or be part of a group or cluster of computing devices networked together to provide greater processing capability.

While the foregoing is directed to embodiments described herein, other and further embodiments may be devised without departing from the basic scope thereof. For example, aspects of the present disclosure may be implemented in hardware or software or a combination of hardware and software. One embodiment described herein may be implemented as a program product for use with a computer system. The program(s) of the program product define functions of the embodiments (including the methods described herein) and can be contained on a variety of computer-readable storage media. Illustrative computer-readable storage media include, but are not limited to: (i) non-writable storage media (e.g., read-only memory (ROM) devices within a computer, such as CD-ROM disks readably by a CD-ROM drive, flash memory, ROM chips, or any type of solid-state non-volatile memory) on which information is permanently stored; and (ii) writable storage media (e.g., floppy disks within a diskette drive or hard-disk drive or any type of solid state random-access memory) on which alterable information is stored. Such computer-readable storage media, when carrying computer-readable instructions that direct the functions of the disclosed embodiments, are embodiments of the present disclosure.

It will be appreciated to those skilled in the art that the preceding examples are exemplary and not limiting. It is intended that all permutations, enhancements, equivalents, and improvements thereto are apparent to those skilled in the art upon a reading of the specification and a study of the drawings are included within the true spirit and scope of the present disclosure. It is therefore intended that the following appended claims include all such modifications, permutations, and equivalents as fall within the true spirit and scope of these teachings.

The invention claimed is:

1. A controlled growth system, comprising:
a controller configured to manage process parameters of a controlled growth environment;
a sensor configured to monitor a biologic in the controlled growth environment during a growth process; and
a computing system in communication with the sensor and the controller, the computing system programmed to perform operations comprising:
initiating the growth process by providing the controller with an initial set of process parameters for the controlled growth environment;
receiving sensor data from the sensor during the growth process, wherein the sensor data comprises at least an image of the biologic;
generating, based on the image, a predicted final quality metric for the biologic, wherein the predicted final quality metric represents a final state of the biologic at an end of the growth process based on a current state of the biologic;
determining that the predicted final quality metric for the biologic is not within a threshold range of a canonical final quality metric;
based on the determining, generating an updated set of process parameters to achieve the canonical final quality metric; and
providing the updated set of process parameters to the controller.

2. The controlled growth system of claim 1, wherein the sensor data further comprises one or more of a temperature reading, a humidity reading, a light intensity reading, and a carbon dioxide level reading.

3. The controlled growth system of claim 1, wherein generating, based on the image, the predicted final quality metric for the biologic comprises:
applying a topographic analysis approach to the biologic to generate the predicted final quality metric.

4. The controlled growth system of claim 1, wherein generating, based on the image, the predicted final quality metric for the biologic comprises:
applying one or more computer vision techniques to the biologic to generate the predicted final quality metric.

5. The controlled growth system of claim 1, wherein generating, based on the image, the predicted final quality metric for the biologic comprises:
inputting the image into a convolutional neural network; and
receiving, as output, the predicted final quality metric for the biologic.

6. The controlled growth system of claim 5, wherein generating the updated set of process parameters to achieve the canonical final quality metric comprises:
outputting, from the convolutional neural network, the updated set of process parameters to achieve the canonical final quality metric based on the current state of the biologic.

7. The controlled growth system of claim 5, further comprising:
training the convolutional neural network to learn how various process parameters affect a final quality metric of the biologic at various stages of growth based on a training data set comprising training images of training biologics and training process parameters of the controlled growth environment corresponding to training image.

8. A method for controlling a growth of a biologic in a controlled growth environment, comprising:
initiating, by a computing system, a growth process for the biologic in the controlled growth environment by providing a controller of the controlled growth environment with an initial set of process parameters;
receiving, by the computing system, sensor data from a sensor of the controlled growth environment during the growth process, wherein the sensor data comprises at least an image of the biologic;
generating, by the computing system, based on the image, a predicted final quality metric for the biologic, wherein the predicted final quality metric represents a final state of the biologic at an end of the growth process based on a current state of the biologic;
determining, by the computing system, that the predicted final quality metric for the biologic is not within a threshold range of a canonical final quality metric;
based on the determining, generating, by the computing system, an updated set of process parameters to achieve the canonical final quality metric; and
providing, by the computing system, the updated set of process parameters to the controller.

9. The method of claim 8, wherein the sensor data further comprises one or more of a temperature reading, a humidity reading, a light intensity reading, and a carbon dioxide level reading.

10. The method of claim 8, wherein generating, based on the image, the predicted final quality metric for the biologic comprises:
applying a topographic analysis approach to the biologic to generate the predicted final quality metric.

11. The method of claim 8, wherein generating, based on the image, the predicted final quality metric for the biologic comprises:
applying one or more computer vision techniques to the biologic to generate the predicted final quality metric.

12. The method of claim 8, wherein generating, based on the image, the predicted final quality metric for the biologic comprises:
inputting the image into a convolutional neural network; and
receiving, as output, the predicted final quality metric for the biologic.

13. The method of claim 12, wherein generating the updated set of process parameters to achieve the canonical final quality metric comprises:
outputting, from the convolutional neural network, the update set of process parameters to achieve the canonical final quality metric based on the current state of the biologic.

14. The method of claim 12, further comprising:
training the convolutional neural network to learn how various process parameters affect a final quality metric of the biologic at various stages of growth based on a training data set comprising training images of training biologics and training process parameters of the controlled growth environment corresponding to training image.

15. A controlled growth system for mycelium, comprising:
a sensor configured to monitor a mycelium sheet in a controlled growth environment during a growth process; and
a computing system in communication with the sensor and the controlled growth environment, the computing system programmed to perform operations comprising:
initiating the growth process by providing the controlled growth environment with an initial set of process parameters for the controlled growth environment;
receiving sensor data from the sensor during the growth process, wherein the sensor data comprises at least an image of the mycelium sheet;
generating, based on the image, a predicted final quality metric for the mycelium sheet, wherein the predicted final quality metric represents a final state of the mycelium sheet at an end of the growth process based on a current state of the mycelium sheet;
determining that the predicted final quality metric for the mycelium sheet is not within a threshold range of a canonical final quality metric;
based on the determining, generating an updated set of process parameters to achieve the canonical final quality metric; and
adjusting the controlled growth environment based on the updated set of process parameters.

16. The controlled growth system of claim 15, wherein the sensor data further comprises one or more of a temperature reading, a humidity reading, a light intensity reading, and a carbon dioxide level reading.

17. The controlled growth system of claim 15, wherein generating, based on the image, the predicted final quality metric for the mycelium sheet comprises:
applying a topographic analysis approach to the mycelium sheet to generate the predicted final quality metric.

18. The controlled growth system of claim 15, wherein generating, based on the image, the predicted final quality metric for the mycelium sheet comprises:
applying one or more computer vision techniques to the mycelium sheet to generate the predicted final quality metric.

19. The controlled growth system of claim 15, wherein generating, based on the image, the predicted final quality metric for the mycelium sheet comprises:
inputting the image into a convolutional neural network; and
receiving, as output, the predicted final quality metric for the mycelium sheet.

20. The controlled growth system of claim 19, further comprising:
training the convolutional neural network to learn how various process parameters affect a final quality metric of the mycelium sheet at various stages of growth based on a training data set comprising training images of training mycelium sheets and training process parameters of the controlled growth environment corresponding to training image.

* * * * *